(12) United States Patent
Chou et al.

(10) Patent No.: US 7,190,013 B2
(45) Date of Patent: Mar. 13, 2007

(54) ISFET USING PBTIO₃ AS SENSING FILM

(75) Inventors: Jung-Chuan Chou, Yunlin Hsien (TW); Wen Yuan Liu, Taoyuan (TW); Wen Bin Hong, Caotun Township, Nantou County (TW)

(73) Assignee: National Yulin University of Science and Technology, Yunlin Hsien (TW)

( * ) Notice: Subject to any disclaimer, the term of this patent is extended or adjusted under 35 U.S.C. 154(b) by 276 days.

(21) Appl. No.: 10/778,285

(22) Filed: Feb. 13, 2004

(65) Prior Publication Data

US 2005/0179065 A1   Aug. 18, 2005

(51) Int. Cl.
*H01L 29/76* (2006.01)
*H01L 29/94* (2006.01)
*H01L 31/00* (2006.01)

(52) U.S. Cl. ............... 257/295; 257/288; 438/3; 438/197

(58) Field of Classification Search ........ 257/288, 257/286, 257, 279, 253, 262, 252, 410–411, 257/414, 295, 306, 309, 314; 438/3, 197, 438/244, 253, 387, 396, 201, 211, 257

See application file for complete search history.

(56) References Cited

U.S. PATENT DOCUMENTS

| 6,784,473 B2 * | 8/2004 | Sakai et al. ............ 257/295 |
| 2002/0195683 A1 * | 12/2002 | Kim et al. ............ 257/532 |
| 2003/0201435 A1 * | 10/2003 | Suzawa ............ 257/59 |

* cited by examiner

*Primary Examiner*—Zandra V. Smith
*Assistant Examiner*—Thanh Y. Tran
(74) *Attorney, Agent, or Firm*—Thomas, Kayden, Horstemeyer & Risley

(57) ABSTRACT

A $PbTiO_3/SiO_2$-gated ISFET device comprising a $PbTiO_3$ thin film as $H^+$-sensing film, and a method of forming the same. The $PbTiO_3$ thin film is formed through a sol-gel process which offers many advantages, such as, low processing temperature, easy control of the composition of the film and easy coating over a large substrate. The $PbTiO_3/SiO_2$ gated ISFET device of the present invention is highly sensitive in aqueous solution, and particularly in acidic aqueous solution. The sensitivity of the present ISFET ranges from 50 to 58 mV/pH. In addition, the disclosed ISFET has high linearity. Accordingly, the disclosed ISFET can be used to detect effluent.

14 Claims, 6 Drawing Sheets

ISFET USING PBTIO₃ AS SENSING FILM

BACKGROUND OF THE INVENTION

1. Field of the Invention

The invention relates to an ion sensitive field effect transistor (ISFET), and in particular to a $PbTiO_3/SiO_2$-gated ISFET device fabricated through a sol-gel process to detect hydrogen ions in an aqueous solution. The invention also relates to a method for forming a sensing film for fabrication of a $PbTiO_3/SiO_2$-gated ISFET device.

2. Description of the Related Art

The ion sensitive field effect transistor (ISFET) is constructed by substituting a sensing film for the metal gate on the gate oxide of a traditional MOSFET. When the ISFET is dipped into a solution, the interfacial potential between the sensing film and the solution will influence the semiconductor surface since only an extremely thin dielectric (that is, the gate oxide) separates the sensing film and the semiconductor surface. This influences the charge density in the inversion layer of the semiconductor surface, and thereby modulates the channel current passing through the ISFET. Therefore, by utilizing this characteristic, the pH value or other ion concentration in the solution can be deduced from the measurement of source/drain current and the gate voltage of the ISFET. Furthermore, the potential difference on the interface between the sensing film and the solution is in relation to the ion activity in the solution. The hydrogen ion activity in the solution can be measured by using different channel currents caused by different interfacial potential differences in various solutions with different hydrogen ion activity.

The patents, which are related to the formation of the ISFET or the measurement of the ISFET, are listed hereinafter.

(1) U.S. Pat. No. 6,531,858 B2 issued to the same inventor, Chou, J. C. and Tsai, H. M., discloses a method of measuring the hysteresis value and the drift value of an a-Si:H ISFET.

(2) U.S. Pat. No. 6,573,741 B2 issued to the same inventor, Chou, J. C., and Wang, Y. F. discloses a method and an apparatus for measuring the temperature parameters of an ISFET that uses hydrogenated amorphous silicon as a sensing film. The method uses the measurements of the temperature parameters and the source/drain current and gate voltage in an unknown solution to sense the ion concentration and the pH value of the unknown solution.

(3) U.S. Pat. No. 5,387,328 issued to Sohn, B. K. discloses a method of measuring the glucose concentration by fixing the enzyme on a sensing film and using platinum (Pt) as a reference electrode. The sensor has a Pt electrode being capable of sensing all biological substances which generate $H_2O_2$ in enzyme reaction.

(4) U.S. Pat. No. 5,319,226 issued to Sohn, B. K. and Kwon, D. H. discloses a $Ta_2O_5$ sensing film deposited by a radio frequency sputtering method on an ISFET, wherein the ISFET consists of a $Ta_2O_5/Si_3N_4/SiO_2$ structure. In this case, a $Ta_2O_5$ film with a thickness between 400 and 500 Å is formed on a $Si_3N_4/SiO_2$ dielectric layer, and the $Ta_2O_5$ film outside the gate is removed by a lift-off process utilizing a positive PR film. Compared with the traditional pH-ISFET, this invention provides better sensitivity and reliability.

(5) U.S. Pat. No. 5,314,833 issued to Lee, K. H.; Cho, K. I.; and Lee, Y. T. discloses a method comprising steps of depositing a silicon film on a GaAs substrate and doping arsenic/phosphorous ions into the silicon film to fabricate the gate with lower resistance. This can reduce the thermal effect on the device, and improve operational characteristics.

(6) U.S. Pat. No. 6,617,190 B2 issued to the same inventor, Chou, J. C., and Chiang, J. L. discloses an ISFET comprising an $H^+$-sensing membrane consisting of RF-sputtering a-$WO_3$. The a-$WO_3/SiO_2$-gated ISFET is highly sensitive in aqueous solutions, and particularly in acidic aqueous solutions, having sensitivity ranging from 50 to 58 mV/pH and high linearity. Accordingly, the ISFET can be also used to detect an effluent.

(7) U.S. Pat. No. 5,061,976 issued to Shimomura T.; Yamaguchi S.; Suzuki T.; and Oyama N. discloses a method that covers a carbon thin film on the gate oxide of the ISFET and then covers a 2, 6-xylenol electrolytically polymerized film thereon. The ISFET has the ability to sense hydrogen ions and the advantages of short drift time, high reliability and insensitivity to light. When particular thin films cover the ISFET, particular kinds of ions can be detected.

(8) U.S. Pat. No. 4,660,063 issued to Anthony, T. R. discloses a method of performing both laser drilling and solid diffusion to form a three-D diode array on a semiconductor wafer. The laser is first employed to drill the wafer, and then the impurities are diffused from the hole to form a cylindrical PN junction, forming a non-plane ISFET structure.

(9) U.S. Pat. No. 4,735,702 issued to Anthony, T. R. provides a polymer covered on an oxide layer of ISFET, wherein a chemical bond is formed on the interface between the polymer and the oxide layer to form a sensitive film.

(10) U.S. Pat. No. 5,911,873 issued to McCarron, R. T. and Gray, J. R. discloses a device that comprises ISFET, a reference electrode device, ISFET control circuits, memory, measuring circuits and diagnostic circuits to measure ion concentration in the solution. The ISFET control circuits operate the equipment at a certain drain/source voltage and a gate/source voltage that is relative to n successive drain currents. The memory stores the repetitions of the ISFET characteristics, the n successive drain currents, and gate/source voltage. The measuring circuits measure ion concentration by a group of the n successive drain currents and a gate/source voltage and the repetition of the ISFET characteristics. The diagnostic circuits measure the ISFET characteristics by using the n successive drain currents and gate/source voltage.

An ISFET using a $PbTiO_3$ layer as a sensing film to detect $H^+$ ions and the fabrication of the $PbTiO_3$ sensing film by a Sol-Gel process have not been disclosed.

SUMMARY OF THE INVENTION

Accordingly, an object of the invention is to provide a $PbTiO_3/SiO_2$ gated ISFET device comprising an $H^+$-sensitive material consisting of $PbTiO_3$. The present ISFET is highly sensitive in solutions, and particularly in acidic solutions, and has sensitivity ranging from 55 to 58 mV/pH, as well as a high linearity. Accordingly, the ISFET of the present invention is capable of detecting $H^+$ ions in an effluent.

Another object of the invention is to provide a method for forming a sensing film.

Still another object of the invention is to provide a method for fabricating a $PbTiO_3/SiO_2$-gated ISFET device.

In order to achieve one object of the invention, the $PbTiO_3/SiO_2$ gated ISFET device is provided, which comprises a semiconductor substrate, a gate oxide layer on the semiconductor substrate, a $PbTiO_3$ layer overlying the gate oxide layer to form a $PbTiO_3$ gate, a pair of source/drain regions in the semiconductor substrate oppositely adjacent to the PbTiO$_3$ gate, two metal wires on the source/drain regions, and a sealing layer overlying the metal wire, and exposing the PbTiO$_3$ layer.

In order to achieve another object of the invention, the method of forming a sensing film is provided. The method comprises the steps of forming a powder of lead acetate hydrate and 1,3-propanediol in a molar ratio of 1:5 in a solvent; heating the solution and cooling the solution to form powder; adding titanium diisopropoxide in a molar ratio of 1:1 to the powder to form a mixture and heating the mixture, and cooling the mixture, thereby achieving homogeneity; refluxing the mixture and cooling the mixture; and spin-coating the mixture on a surface and performing a pyrosol process on the mixture; thereby forming a PbTiO$_3$ thin film as a sensing film.

In order to achieve the still another object of the invention, the method of fabricating a PbTiO$_3$/SiO$_2$-gated ISFET device is provided. A gel is formed into a film overlying the gate oxide layer of a portion of a transistor and performing a pyrosol process on the film to form a PbTiO$_3$ layer as a PbTiO$_3$ gate. The transistor portion comprises a semiconductor substrate, a gate oxide layer on the semiconductor substrate, and source/drain regions in the semiconductor substrate. The gel is a mixture obtained from the steps as described in the method of forming a sensing film. Metal wires connect to the source/drain regions and a sealing layer overlying the metal wire is formed to seal the device but leave the PbTiO$_3$ gate exposed, thereby producing the PbTiO$_3$/SiO$_2$-gated ISFET device.

The PbTiO$_3$ thin film used as a sensing film is novel. Moreover, the PbTiO$_3$ thin film is fabricated by the sol-gel technology. The sol-gel technique offers many advantages over other processing technologies, such as, low processing temperature, easy control of the composition of the film and easy coating for large substrates.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
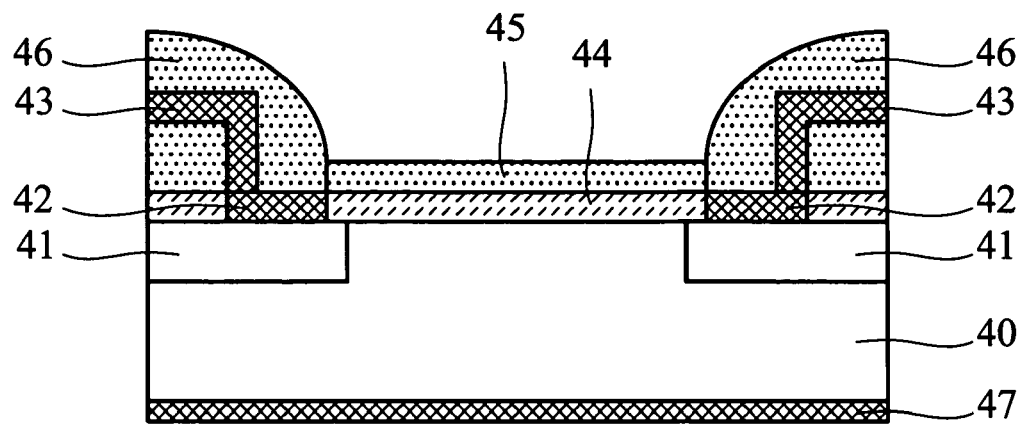
FIG. 1 shows a cross-section schematic diagram of the PbTiO$_3$ ISFET according to the present invention.

FIG. 1 shows a cross-sectional schematic diagram of the PbTiO$_3$/SiO$_2$-gated ISFET device according to the present invention. The PbTiO$_3$ ISFET is formed on a semiconductor substrate 40, preferably a p-type silicon substrate. A pair of source/drain regions 41 approach the top surface of the semiconductor substrate 40 and connect to a constant voltage/current circuit through a pair of contact layers 42 and metal lines 43. On the surface of the semiconductor substrate 40 between the two source/drain regions 41, a gate oxide layer 44 comprising silicon oxide is formed. A PbTiO$_3$ sensing film 45 is formed on the gate oxide layer 44. A sealing layer 46 seals the device but leave the PbTiO$_3$ sensing film 45 exposed. Furthermore, an aluminum layer 47 is formed at the bottom of the semiconductor substrate 40 to reduce the channel-adjusting effect.

In an embodiment of the present invention, the width of the channel, the length of the channel, and the ratio of width/length of the channel of the ISFET are about 1000 μm, 50 μm and 20, respectively. The semiconductor substrate is P-type with a resistivity ranging from about 8 to 12 Ω·cm. Moreover, the lattice parameter of the semiconductor is preferably (1,0,0). The thickness of the gate oxide is about 1000 Å, and the thickness of the PbTiO$_3$ sensing film is 0.25 to 0.75 μm, preferably 0.45 to 0.55 μm. The metal wire may comprise aluminum. The sealing layer may comprise epoxide resin. The source/drain is preferably N-type, which may comprise phosphorous. The PbTiO$_3$ layer is preferably formed on the gate oxide layer by spin coating.

The present invention also provides a method of forming a sensing film. Lead acetate hydrate and 1,3-propanediol are first mixed in a molar ratio of 1:5 in a solvent to form a solution. The solvent can be any solvent as long as it can dissolve the mixture of lead acetate hydrate and 1,3-propanediol. One example of the solvent is 1,3-propandiol. The solution is heated at 135 to 145° C., preferably 138 to 142° C., for 25 to 35 minutes, preferably 30 minutes, and then cooled to 75 to 85° C., preferably 80° C., resulting in a powder. Titanium diisopropoxide in a molar ratio of 1:1 is added to the powder to form a mixture. The mixture is heated at 115 to 125° C., preferably 120° C., for 55 to 65 minutes, preferably 30 minutes and then cooled to 75 to 85° C. in order to form a homogeneous mixture. The mixture is refluxed at 75 to 85° C., preferably 80° C., for 115 to 125 minutes, preferably 120 minutes and then cooled to room temperature, forming a gel. The gel is formed into a film on a surface, such as a silicon surface or a silicone dioxide surface. The methods of forming a film can be spray coating, dip coating, spin coating, and the like. Among them, spin coating can achieve a relatively uniform film thickness. Subsequently, the resulting film is subjected to a pyrosol process at 340 to 360° C., preferably 345 to 355° C., to form a PbTiO$_3$ thin film which can act as a sensing film to sense H$^+$ ion. The film coating and the pyrosol process can be performed repeatedly on the surface to form a multilayer structure as desired. In an embodiment of the present invention, the PbTiO$_3$ thin film is formed on the top surface of a gate oxide layer of a transistor to form a PbTiO$_3$/SiO$_2$ gated ISFET device, suitably as a pH-sensing device. The thickness of the PbTiO$_3$ thin film is preferably 0.25 to 0.75 μm, more preferably 0.45 to 0.55 μm.

EMBODIMENT AND TEST

An ISFET using $PbTiO_3$ as a sensing film was fabricated according to the present invention. A P-type (1,0,0) semiconductor substrate 100 with a resistivity ranging from 8 to 12 Ω·cm was first provided. A pad oxide layer consisting of silicon dioxide with a thickness of 5000 Å was formed on the substrate 100 by wet-oxidation. A first photoresist pattern was formed on the pad oxide layer by conventional photolithography. Using the photoresist pattern as a mask, a dummy gate used to define the subsequent gate area was formed by removing a portion of the pad oxide layer. Then, using the dummy gate as a mask, impurities were implanted into the semiconductor substrate to form a source/drain oppositely adjacent to the dummy gate. The impurities implanted herein were phosphorous ions with a dose of $10^{15}$ $cm^{-2}$. The dummy gate was removed, that is, the pad oxide layer and the first photoresist pattern were removed by wet-etching. An insulating layer consisting of silicon dioxide with a thickness of about 1000 Å was formed on the semiconductor substrate 100. A second photoresist pattern (PR) was formed on the insulating layer by photolithography. Then, using the second photoresist pattern as a mask, the insulating layer outside the gate area was removed. The residual insulating layer within the gate area was used as a gate oxide layer. Subsequently, the second photoresist layer was removed. Thus, the transistor portion was obtained.

A gel was formed by the following steps. A solution of lead acetate hydrate and 1,3-propanediol in a molar ratio of 1:5 was heated at 120° C. for 1 hour and cooled to 80° C. to form powder. Titanium diisopropoxide was added in a molar ratio of 1:1 to the powder to form a mixture and heated at 120° C. for 1 hour, and cooled down to 80° C., forming a homogeneous mixture. The mixture was refluxed at 80° C. for 2 hours and cooled down to room temperature, forming the gel.

Then, the gel was spin coated on the gate oxide layer of the transistor, dried at 150° C., and heated at 350 to 400° C. for 1 hour to form a $PbTiO_3$ thin film on the gate oxide layer. Aluminum wires were used to connect the drain/source areas. The entire ISFET device except the surface of the $PbTiO_3$ layer was covered with epoxide resin and heated to cure the epoxide resin, obtaining a $PbTiO_3/SiO_2$ gated ISFET device.

The obtained $PbTiO_3/SiO_2$ gated ISFET had a channel length of about 50 μm and a channel width of about 1000 μm. Thus, the aspect ratio (i.e. channel width/channel length) of the $PbTiO_3/SiO_2$ gated ISFET was 20. The $PbTiO_3/SiO_2$ gated ISFET device was tested and is described hereinafter.

Figure 2:
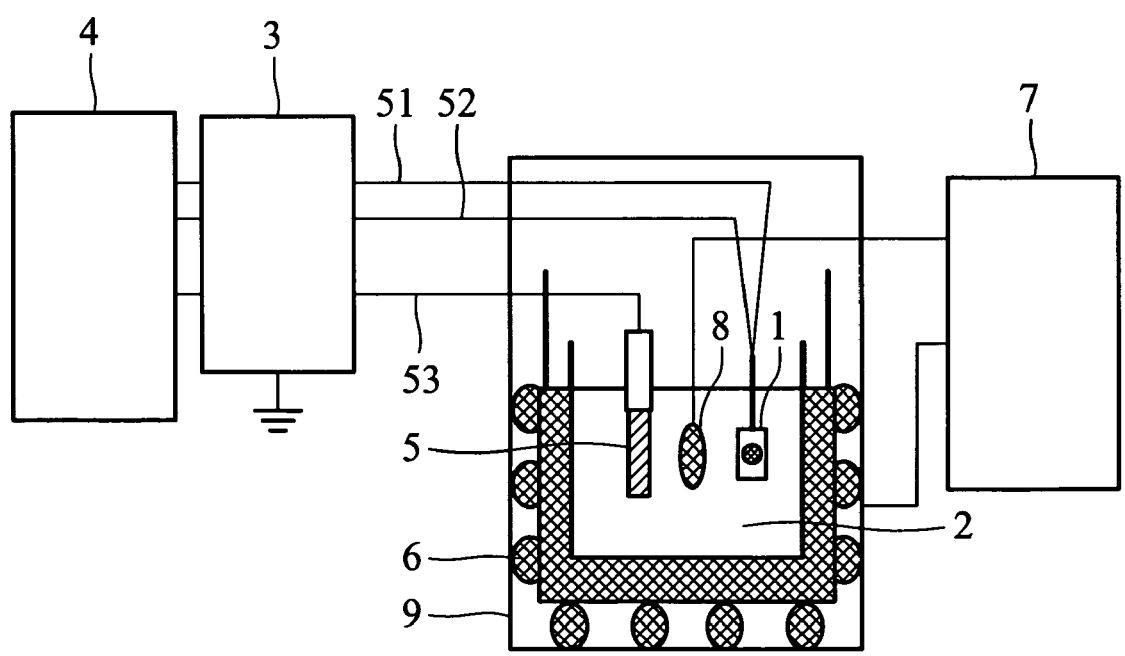
FIG. 2 shows a current-voltage systematic structure diagram according to the present invention.

Please refer to FIG. 2. FIG. 2 shows a systematic structure diagram according to the invention. An ISFET using $PbTiO_3$ as a sensing film (herein referred to "$PbTiO_3/SiO_2$-gated ISFET") 1 was dipped into a buffer solution 2 such as the phosphate buffer solution that was stored in a container (not labeled). The source/drain (not shown) of the $PbTiO_3/SiO_2$-gated-ISFET 1 respectively connected to a test fixture 3 through two connecting wires 51 and 52 to convey the electrical signals obtained by measuring the source/drain to a current/voltage measuring device 4. The current/voltage measuring device 4 was the Keithley-236 current/voltage measuring device for data processing.

A reference electrode 5 was also dipped into the buffer solution 2, and one end of the reference electrode 5 was connected with the test fixture 3 through the connecting wire 53. A heater 6 was installed outside the container and connected with a PID temperature controller 7. When the temperature of the buffer solution 2 was rising or descending, the PID temperature controller 7 controlled the heater 6 to stop or start heating. A thermal couple 8 connected with the PID temperature controller 7 contacted the buffer solution 2 and sensed the temperature thereof. The previously mentioned elements such as the buffer solution 2, the elements contacting the buffer solution 2 and the heater 6 were placed in a light-isolation container (a dark chamber) 9 to prevent the measuring data from being affected by light. It should be noted that in the preferred embodiment of the invention the interfacial potential between the $PbTiO_3$ sensing film and the solution and the characteristic difference of charge density in the inversion layer of the semiconductor surface were used to measure required data (such as the source/drain current or the gate voltage) and thus obtained the temperature parameters of the ISFET.

Figure 3:
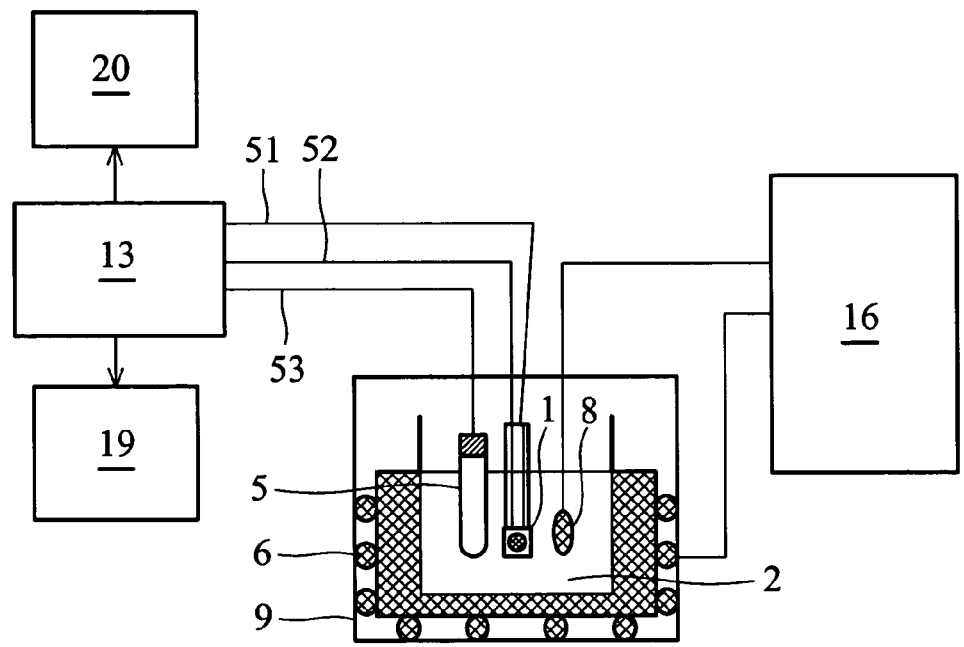
FIG. 3 shows a hysteresis systematic structure diagram according to the present invention.

FIG. 3 shows a schematic diagram according to the present invention. An ISFET 1 using the $PbTiO_3$ thin film as a sensing film (called $PbTiO_3/SiO_2$ ISFET) to detect $H^+$ ions was dipped into a buffer solution 2 composed of a standard buffer solution and carried by a container (not labeled). A drain/source (not shown) of the $PbTiO_3$ ISFET 1 was connected to a constant voltage/current circuit 13 (such as a negative feedback circuit) through two wires 51, 52. The constant voltage/current circuit 13 was utilized to fix the drain/source voltage and the drain/source current of the $PbTiO_3$ ISFET 1.

A reference electrode 5 was installed in the buffer solution 2, wherein one end of the reference electrode 5 was connected to the constant voltage/current circuit 13 through a wire 53. A heater 6 installed outside the container was connected to a PID temperature controller 16. Both the heater 6 and the PID temperature controller 16 were used to maintain the buffer solution 2 at a constant temperature (preferably 25° C.) that was detected by a thermal couple 8 connected to the PID temperature controller 16. The above-mentioned buffer solution 2, every device connected thereto, and the heater 6 were placed in a light-isolation container 9 (preferred as a dark chamber) to reduce the effect of light on the measuring results.

The constant voltage/current circuit 13 was connected to a current/voltage measuring device 19 that comprised two digital multimeters for detecting whether the source/drain current and the source/drain voltage of the $PbTiO_3$ ISFET 1 trended toward stability. The constant voltage/current circuit 13 was also connected to a voltage-time recorder 20 for setting and recording the output voltages during each recording period.

Figure 4:
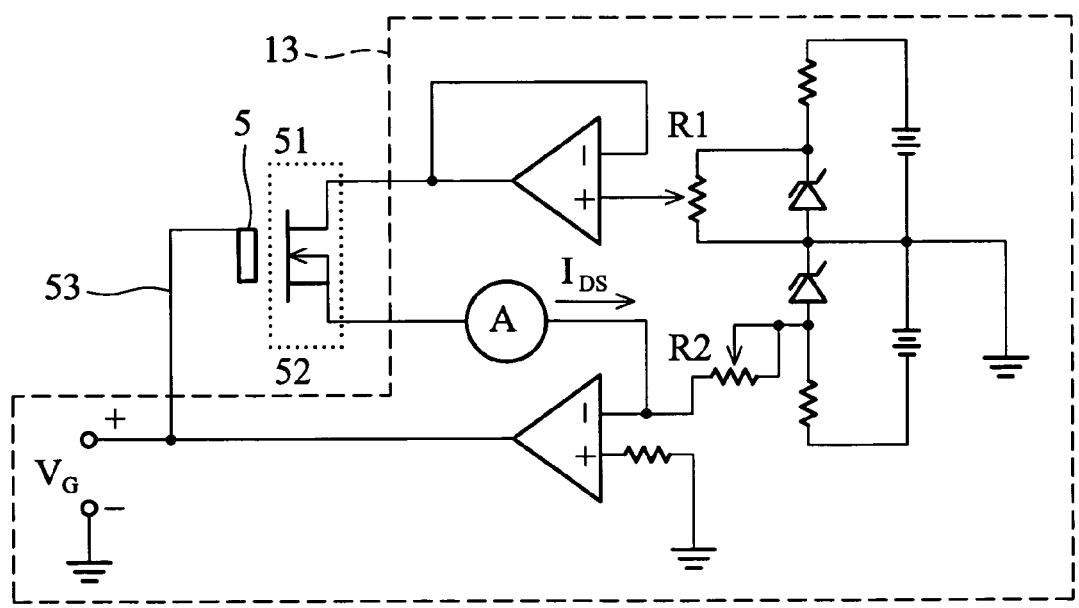
FIG. 4 shows a schematic diagram of the constant voltage/current circuit according to the present invention.

FIG. 4 shows a schematic diagram of the constant voltage/current circuit 13 according to the present invention. The constant voltage/current circuit 13 was connected to the source/drain of the $PbTiO_3$ ISFET 1 through the wires 51, 52, and was connected to the reference electrode 5 through the wire 53. By adjusting the variable resistance R1, the source-drain voltage could be fixed at a constant value (preferred at 0.2 V). By adjusting the variable resistance R2, the source-drain current could be fixed at a constant value (preferred at 70 μA). In the case of negative feedback, when the drain-source current IDS was increased the source voltage, the output voltage and gate voltage were reduced and finally the drain-source current IDS was reduced. The circuit 13 has advantages of simplicity, low cost, and easy operation and does not require adjusting the measuring point of the device.

Figure 5:
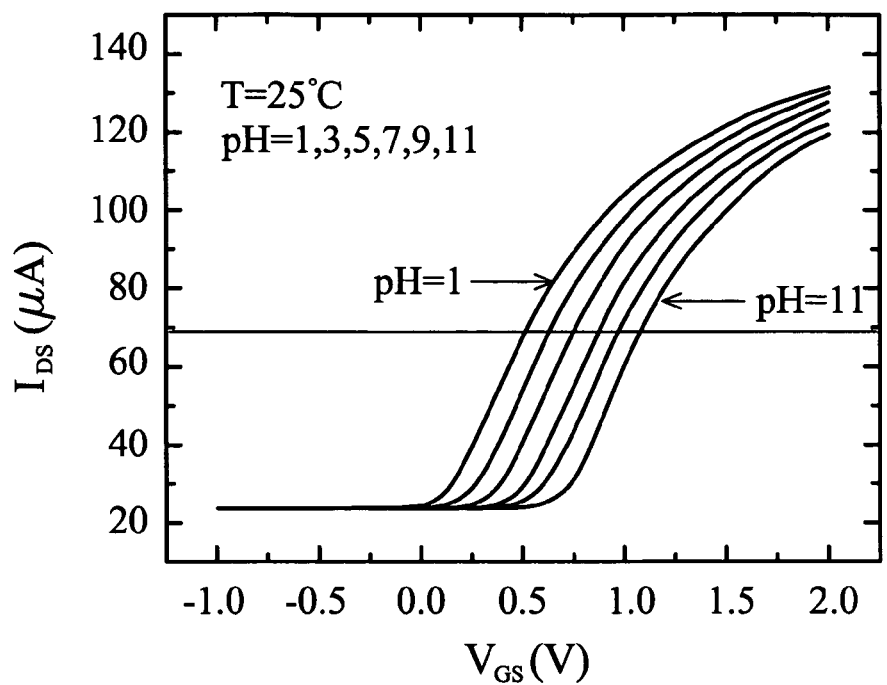
FIG. 5 shows the current-voltage curves of the PbTiO$_3$/SiO$_2$ gated ISFET under various pH values (1, 3, 5, 7, 9, 11)

FIG. 5 shows the current-voltage curves of the Sol-Gel $PbTiO_3/SiO_2$ gated ISFET fabricated according to this invention, wherein the measurement was accomplished by placing the sensing device in the various pH solutions (pH=1, 3, 5, 7, 9, 11) at room temperature. Similarly, the obtained data were analyzed by the semiconductor parameter analyzer (Model HP 4145B). According to FIG. 5, it was found that the threshold voltage linearly increased with the increasing pH value of the aqueous solution when the PbTiO$_3$ sensing membrane was used.

Figure 6:
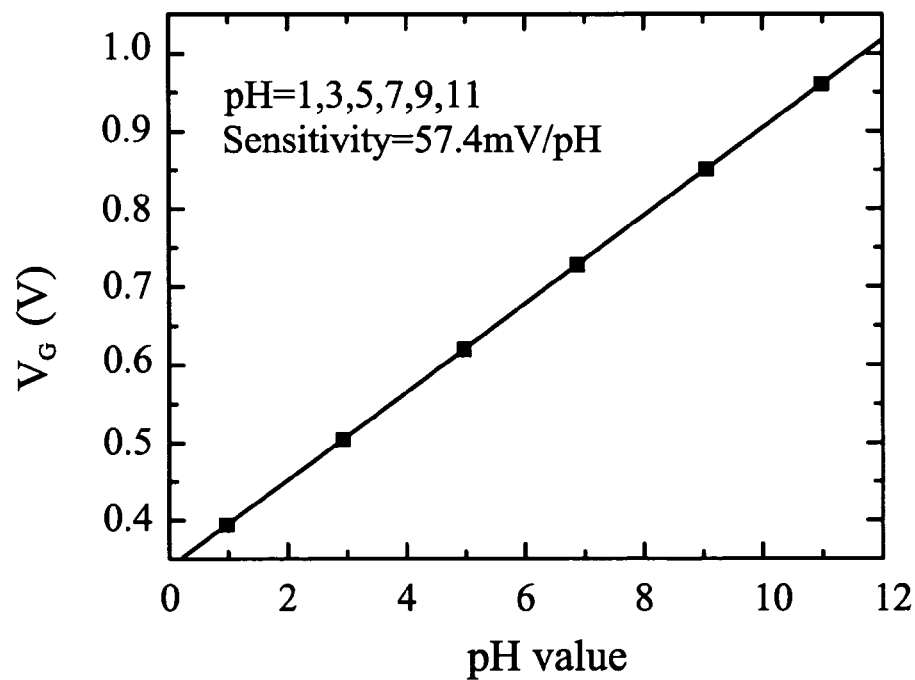
FIG. 6 shows the sensitivity of the PbTiO$_3$/SiO$_2$ gated ISFET under various pH values (1, 3, 5, 7, 9, 11)

FIG. 6 shows the sensitivity of the PbTiO$_3$/SiO$_2$ gate ISFET fabricated according to this invention under various pH values 1, 3, 5, 7, 9, 11. As shown in the FIG. 6, the slope of the curve demonstrated the sensitivity of the sensing device. Accordingly, the sensitivity of the sensing device consisting of PbTiO$_3$/SiO$_2$ was 57.4 mV/pH.

Figure 7:
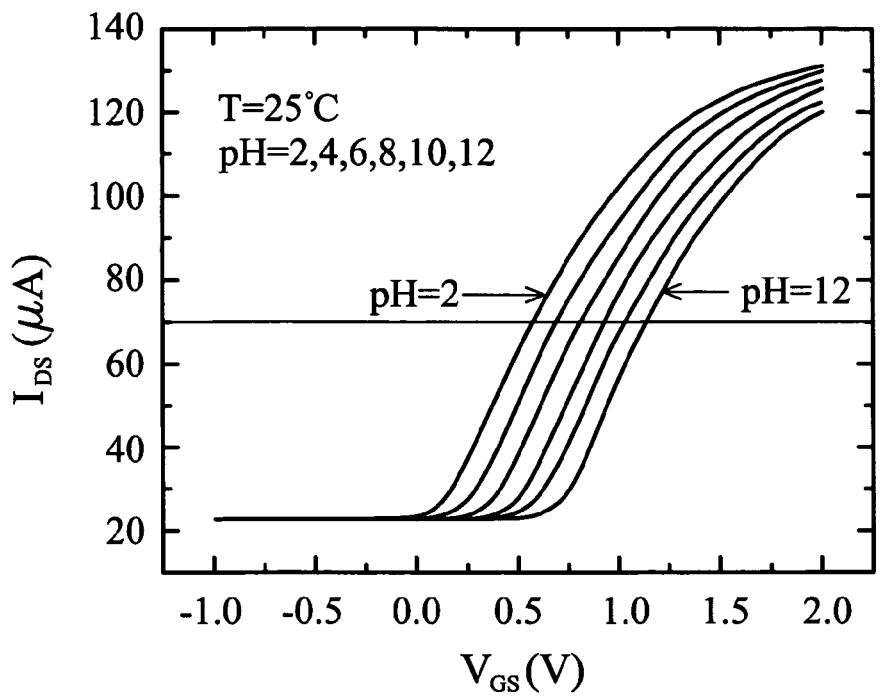
FIG. 7 shows the current-voltage curves of the PbTiO$_3$/SiO$_2$ gated ISFET under various pH values (2, 4, 6, 8, 10, 12)

FIG. 7 shows the current-voltage curves of the sol-gel PbTiO$_3$/SiO$_2$ gated ISFET fabricated according to this invention, wherein the measurement was accomplished by placing the sensing device in the various pH solutions (pH=2, 4, 6, 8, 10, 12) at room temperature. Similarly, the obtained data were analyzed by the semiconductor parameter analyzer (Model HP 4145B). According to FIG. 7, it was found that the threshold voltage linearly increased with the increasing pH value of the aqueous solution when the PbTiO$_3$ sensing membrane was used.

Figure 8:
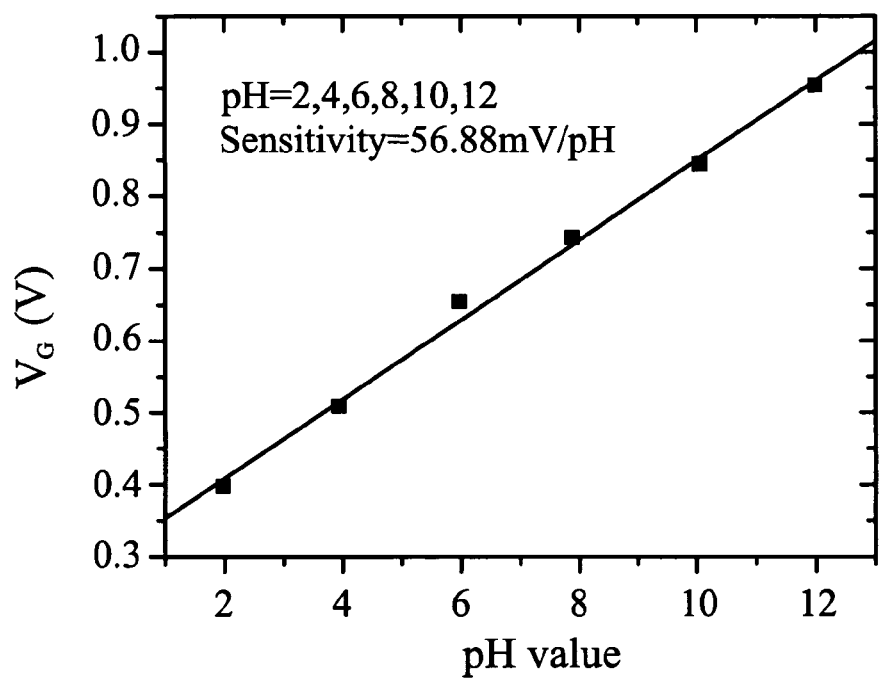
FIG. 8 shows the sensitivity of the PbTiO$_3$/SiO$_2$ gated ISFET under various pH values (2, 4, 6, 8, 10, 12)

FIG. 8 shows the sensitivity of the PbTiO$_3$/SiO$_2$ gated ISFET fabricated according to this invention under various pH values 2, 4, 6, 8, 10, 12). As shown in the FIG. 8, the slope of the curve demonstrated the sensitivity of the sensing device. Accordingly, the sensitivity of the sensing device consisting of PbTiO$_3$/SiO$_2$ was 56.88 mV/pH.

Figure 9:
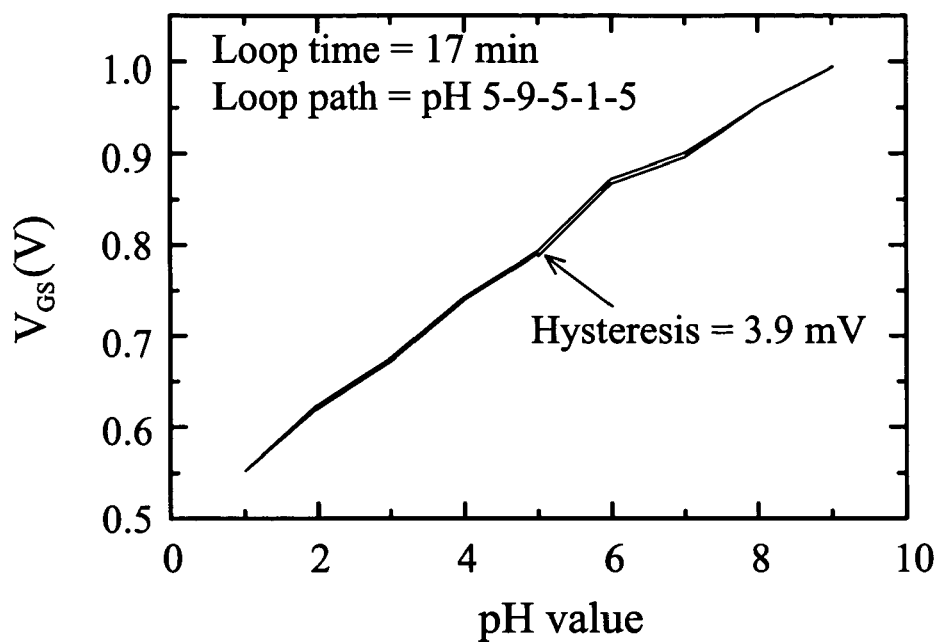
FIG. 9 shows a residual regression diagram for PbTiO$_3$ gate-ISFET at a loop time of 1020 seconds.

According to the above-mentioned measuring method, the measuring results and the pH values are drawn as a residual regression diagram in FIG. 9. It is obvious that the hysteresis value is 3.9 mV when pH value is 5. By using the same method, all of the hysteresis values at different pH values can be determined and aid the reverse compensation method.

With reference to the drift value, the constant voltage/current circuit (negative feedback circuit) was utilized to fix the drain/source current and the drain/source voltage of the PbTiO$_3$ ISFET. The PbTiO$_3$ ISFET and the reference electrode were connected to the constant voltage/current circuit, and then dipped into the solution. By adjusting the variable resistance R1, the VD value was set at 0.2 V by one digital multimeter. Also, by adjusting the variable resistance R2, the IDS value was set by the other digital multimeter. Afterwards, the PbTiO$_3$ ISFET was dipped into the buffer solution for a period of time. The voltage-time recorder was utilized to record the gate/source output voltage of the PbTiO$_3$ ISFET, and thereby measure the drift values.

It should be noted that a current generated by illumination affects the drift value. Hence, the drain-source current should be adjusted to be between 10 µA and more than 100 µA to reduce the illumination effect. Additionally, when the drain-source current is extremely large, the stability is easily affected by temperature. Accordingly, the preferred embodiment set the drain-source current at 10 to 300 µA.

Figure 10:
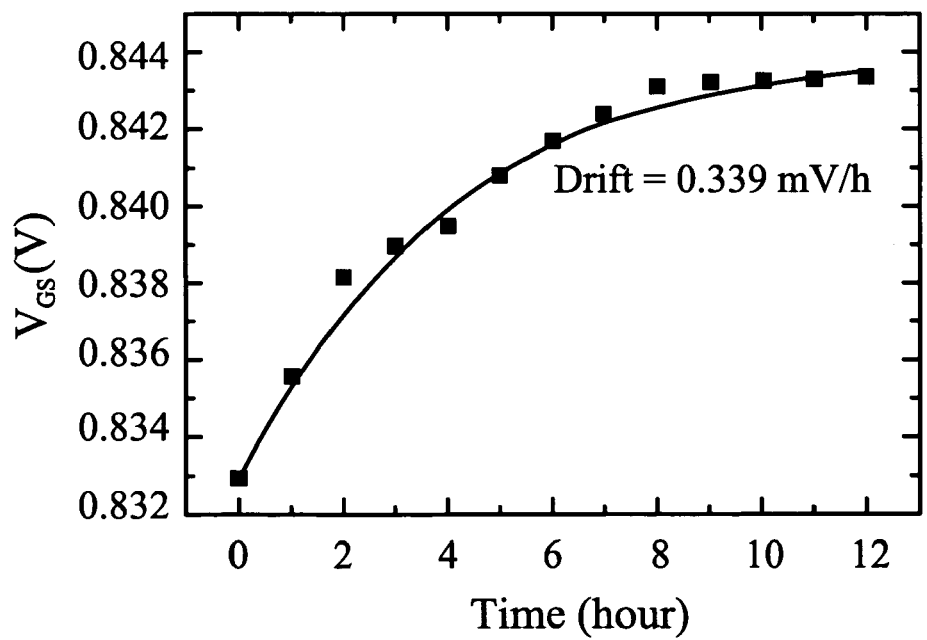
FIG. 10 shows the curve of the gate/source output voltage versus time when the pH value is 7.

FIG. 10 shows curves of the relationship between gate/source output voltage ($V_{GS}$) and time when the pH value is 7. The data are shown in the curve, wherein the data are the experimental results (shown as a line) by using the method of the present invention by using a multiple time-constant model. It is obvious that the simulated result matches the experimental result. The drift value is 0.339 mV/h when $I_{DS}$ is 100 µA, $V_{DS}$ is 0.2V, pH value is 7, and test time is 12 hours. The drift value can be determined from the slope of the curve whose time parameter is more than the twelve hours.

Figure 11:
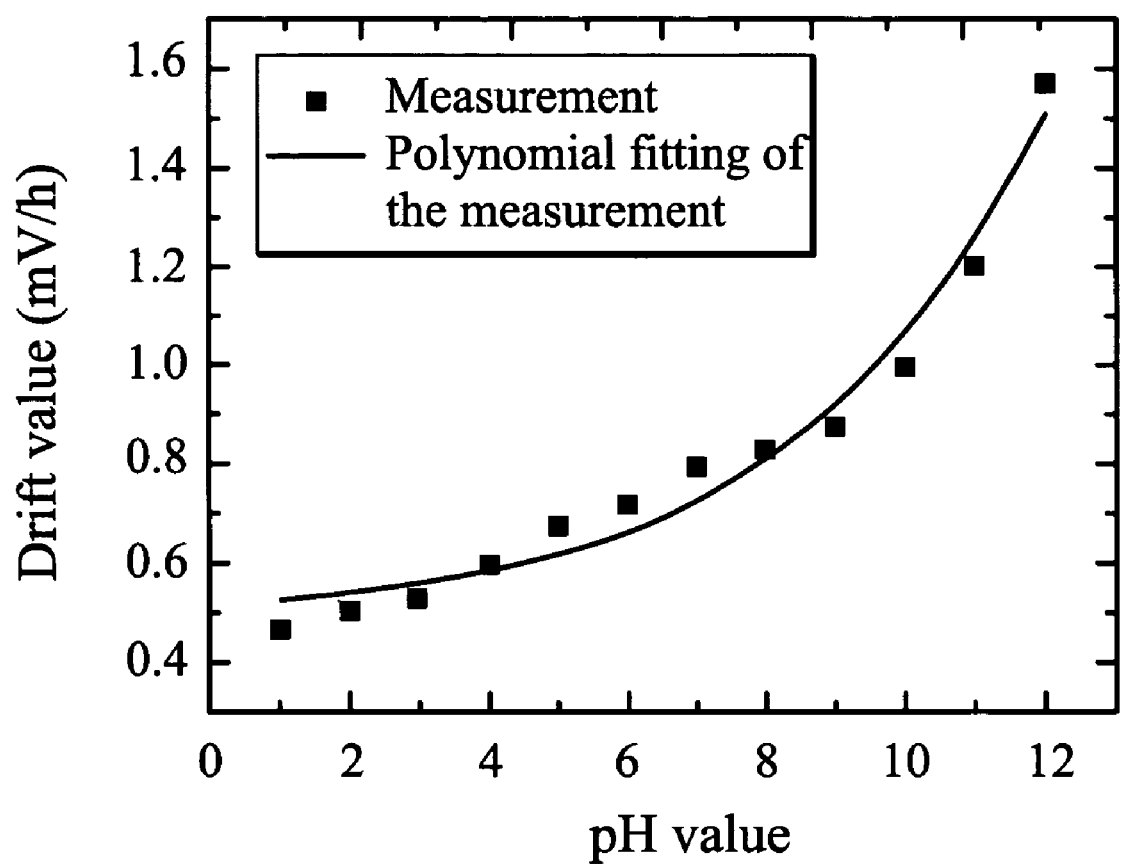
FIG. 11 shows the curve of the drift value versus the pH value.

FIG. 11 shows the relationship between the drift values and the pH values. At pH=1, the drift value is 0.462 mV/h; at pH=2, the drift value is 0.498 mV/h; at pH=3, the drift value is 0.528 mV/h; at pH=4, the drift value is 0.586 mV/h, at pH=5, the drift value is 0.664 mV/h; at pH=6, the drift value is 0.714 mV/h; at pH=7, the drift value is 0.785 mV/h, at pH=8, the drift value is 0.82 mV/h; at pH=9, the drift value is 0.871 mV/h; at pH=10, the drift value is 0.968 mV/h, at pH=11, the drift value is 1.21 mV/h; and at pH=12, the drift value is 1.573 mV/h. According to the data, it is believed that the drift behavior is more obvious when the pH value is greater. Also, when the data approximately form a line, the drift values at any other pH values can be estimated, which is helpful for doing reverse compensation.

Those skilled in the art will readily observe that numerous modifications and alterations of the device may be made while retaining the teaching of the invention. Accordingly, the above disclosure should be constructed as limited only by the metes and bounds of the appended claims.

What is claimed is:

1. A PbTiO3/SiO2 gated ISFET device, comprising:
   a semiconductor substrate;
   a gate oxide layer on the semiconductor substrate;
   a PbTiO$_3$ layer directly contacting the gate oxide layer to form a PbTiO$_3$ gate;
   a pair of source/drain regions in the semiconductor substrate oppositely adjacent to the PbTiO$_3$ gate;
   a pair of metal wires on the source/drain regions; and
   a sealing layer overlying the metal wire, and exposing the PbTiO3 layer,
   wherein a top surface of the PbTiO$_3$ layer is exposed.

2. The device as claimed in claim 1, wherein the width of the channel, the length of the channel and the ratio of width/length of the channel of the ISFET is about 1000 µm, 50 µm, and 20 respectively.

3. The device as claimed in claim 1, wherein the semiconductor substrate is P-type.

4. The device as claimed in claim 1, wherein the resistivity of the semiconductor substrate ranges from 8 to 12 Ω·cm.

5. The device as claimed in claim 1, wherein the lattice parameter of the semiconductor is (1,0,0).

6. The device as claimed in claim 1, wherein the thickness of the gate oxide is about 1000 Å.

7. The device as claimed in claim 1, wherein the metal wire comprises aluminum.

8. The device as claimed in claim 1, wherein the sealing layer comprises epoxide resin.

9. The device as claimed in claim 1, wherein the source/drain is N-type.

10. The device as claimed in claim 1, wherein the PbTiO$_3$ layer is formed on the gate oxide layer by spin coating.

11. The device as claimed in claim 10, wherein the N-type impurities within the source/drain regions comprise phosphorous.

12. The device as claimed in claim 1, wherein the PbTiO$_3$ layer directly contacts the entire gate oxide layer.

13. The device as claimed in claim 1, wherein the PbTiO$_3$ gate consists of the gate oxide layer and the PbTiO$_3$ layer, in which the PbTiO$_3$ layer servers as a gate electrode.

14. The device as claimed in claim 1, wherein the top surface of the PbTiO3 layer is exposed to a solution to detect ions therein.

* * * * *